United States Patent [19]

Lebling et al.

[11] Patent Number: 4,583,858
[45] Date of Patent: Apr. 22, 1986

[54] DEVICE FOR USE IN CHROMATOMETRY OF SAMPLES

[75] Inventors: Karl Lebling, Munich; Helmut Reisser, Vaterstetten, both of Fed. Rep. of Germany; Hendrik J. A. Saris, Bennebroek, Netherlands

[73] Assignee: Deutsche Akzo Coatings & Byk-Mellinckrodt Chemische Products, GmbH, Fed. Rep. of Germany

[21] Appl. No.: 441,054

[22] Filed: Nov. 12, 1982

[30] Foreign Application Priority Data

Nov. 17, 1981 [DE] Fed. Rep. of Germany ....... 3145633

[51] Int. Cl.[4] .............................................. G01J 3/50
[52] U.S. Cl. .................................... 356/402; 356/446
[58] Field of Search ............... 356/402, 445, 446, 447, 356/448

[56] References Cited

U.S. PATENT DOCUMENTS

| | | | |
|---|---|---|---|
| 3,999,864 | 12/1976 | Mutter | 356/448 |
| 4,218,144 | 8/1980 | Whitehouse et al. | 356/446 |
| 4,412,746 | 11/1983 | Yokouchi | 356/446 |

FOREIGN PATENT DOCUMENTS 2101818 1/1971 Fed. Rep. of Germany.

*Primary Examiner*—F. L. Evans
*Attorney, Agent, or Firm*—Barnes & Thornburg

[57] ABSTRACT

The invention relates to a device for use in chromatometry of samples, viz. colored surfaces, by measurement of reflectance. It comprises a testing head having a measuring cell and a measuring surface. The measuring cell is provided in each of five radial planes with three optical fibre bundles for irradiation of the sample, said optical fibre bundles being disposed at three different angles of e.g. 15°, 30° and 70° to the measuring surface. In the center at the top of the measuring cell there is also provided an optical fibre bundle oriented perpendicular to the measuring surface and intended to divert the radiation reflected from the sample. According to the invention a switching system is provided which permits selectively to turn on or off a part of the total number of optical light guide means, especially in accordance with a plurality of preselectable programmes.

The device according to the invention, which comprises a portable testing head, is particularly intended for color measurements of the paint or enamel on passenger car bodies and/or measuring structural paints or enamels and/or such paints containing metal particles.

25 Claims, 8 Drawing Figures

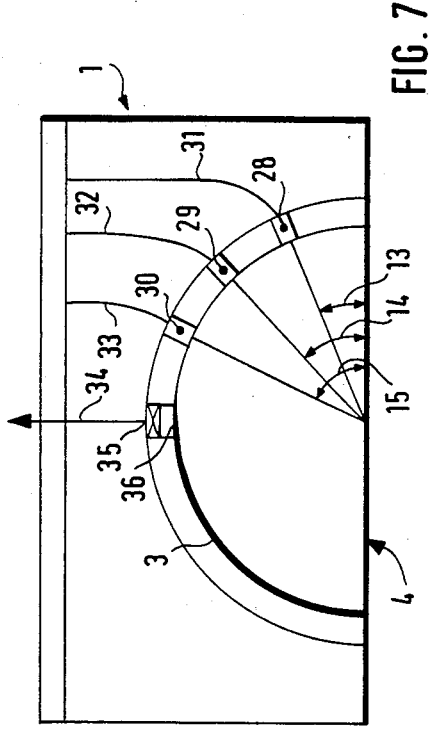
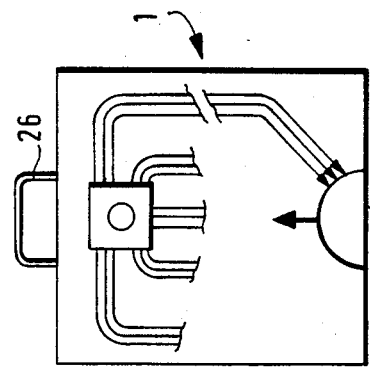
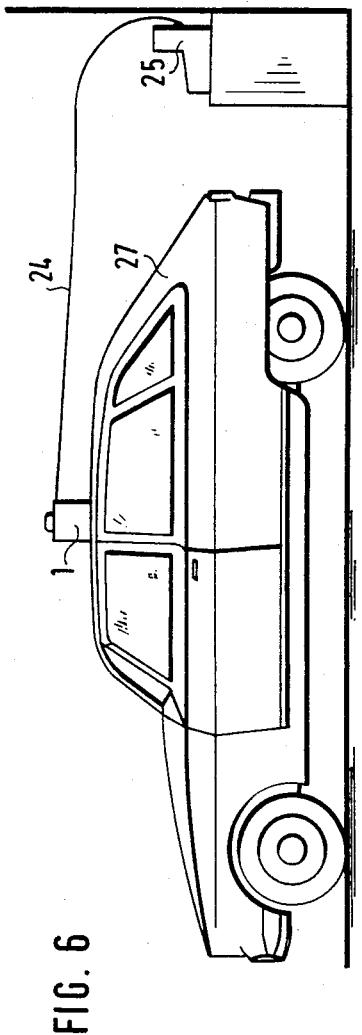
FIG. 7
FIG. 5
FIG. 6

DEVICE FOR USE IN CHROMATOMETRY OF SAMPLES

This invention relates to a device for use in chromatometry of samples, viz. coloured surfaces, comprising a testing head including a measuring cell having a measuring surface, the measuring cell comprising a plurality of optical light guide means disposed at different angles to the measuring surface and in different radial planes for supplying the radiation irradiating said sample and for diverting the radiation reflected from said sample to an analyzing measuring means.

A chromatometer of the above-specified type is disclosed in German Patent Application No. 2,101,818. The examples given in this patent application describe a testing head in which the measuring cell is provided with optical light guide means disposed at an angle of 45° to the measuring surface and in six radial planes for diverting the radiation reflected from the sample to an analyzing measuring means. On page 8 of said patent application it is specified that four other arrangements were recommended in 1967 in addition to a geometry of 45°, and that one geometry may be preferred to the other ones depending on the surface characteristics of the sample under investigation. When using flexible optical light guide means in the configuration of said German patent application it is possible to perform colour measurement for any desired geometry by the use of different scanning heads, wherein the ends of said optical light guide means are disposed at corresponding viewing angles and said heads may be replaced rapidly and easily.

However, such a replacing of testing heads has considerable drawbacks when a certain sample surface is to be irradiated and viewed at different angles. Following the exchange of testing heads it is difficult in the second measuring step to direct the second testing head exactly to the same spot. When this results in a practically unavoidable displacement between the first and the second measurement, the measuring results will be inaccurate. This difficulty becomes extremely serious when the shade of the paint or enamel is to be measured on samples having slightly curved surfaces. These difficulties are still enhanced when the paint surface displays inhomogeneities, structures and irregularities, which is always the case in actual practice.

It is true that it is stated on page 8, last line, of German Patent Application No. 2,101,818 that a combination of more than one geometry, i.e., of a plurality of measuring angles, is also possible. But this has the drawback that it is only possible to irradiate and to view the surface of the sample simultaneously in more than one geometry. Such simultaneous measurement at different angles is, however, insufficient in the colour measurement of samples having structural and curved surfaces and/or having anisotropic surfaces, e.g. metallic paints.

It is the object of the present invention to provide an improved chromatometer which eliminates the above-specified drawbacks of the prior art devices.

The above-specified object is solved by the provision of a device for use in colour measurement of samples, comprising a testing head including a measuring cell having a measuring surface, the measuring cell comprising a plurality of optical light guide means disposed at different angles to the measuring surface and in different radial planes for supplying the radiation irradiating said sample and for diverting the radiation reflected from said sample to an analyzing measuring means, characterized in that it is provided with a switching system which enables part of the total number of said optical light guide means to be selectively turned on or turned off.

In accordance with the present invention the switching system is adapted to turn on or or to turn off either all or part of said optical light guide means disposed at the same angle to said measuring surface. The present invention provides a device comprising n (with $n \geq 2$) optical light guide means disposed at different angles to said measuring surface, characterized in that said switching system is adapted to turn on or to turn off all optical light guide means disposed at 1 to $n-1$ different angles to said measuring surface, either collectively or in any desired combination thereof. Furthermore, the switching system according to the invention permits turning on or turning off of said optical light guide means disposed in one or several radial planes, either collectively or partly. In a preferred embodiment of the invention said optical light guide means are disposed substantially in 3 to 6 different radial planes and at substantially 2 to 6, especially three, different angles to said measuring surface. In a further preferred embodiment of the device according to the invention, an optical light guidemeans for diverting the radiation reflected from said sample is disposed in the centre of said—e.g. semispherical—measuring cell and vertical to said measuring surface, and the remaining optical light guide means are designed to supply the radiation irradiating said sample, said optical light guide means being optical fibre bundles. In a simple embodiment of the device according to the invention, said switching system comprises a switching means to which said optical light guide means are coupled and which is adapted to turn on or to turn off one or several of said optical light guide means or groups of optical light guide means. According to the invention movable auxiliary means is provided for turning on or turning off one or several of said optical light guide means or groups of optical light guide means, said movable auxiliary means being formed by an axially movable envelope—e.g. of cylindrical configuration—disposed between said light source and said optical light guide means and rotatable about its axis, the surface of said envelope being provided with apertures which correspond to the various optical light guide means and switching states.

In a suitable embodiment of the device according to the invention said measuring surface may be directly irradiated, and only a single light source is provided for irradiation, said light source being disposed within said portable testing head and being coupled thereto by means of optical fibre bundles.

In a preferred embodiment of the device according to the invention, said measuring cell is provided for single-beam measurements of only a single object, and the reference object, e.g. a standard ceramic white plate, is disposed either externally or internally of said measuring cell.

In a device according to the invention, in which long-term chromatometric accuracy is ensured, said means for diverting the radiation reflected from the sample is formed by an electric conductor which is mounted on a particular radiation-receiving spot of said measuring cell by way of a converting element for converting optical signals into electric signals.

In an advantageous embodiment of the device according to the invention, said switching system permits turning on or turning off of at least a group of optical light guide means by means of a -possibly preselected- programme.

The device according to the invention, which includes a portable testing head, may be used advantageously for measuring the paint shade on the body of a vehicle, and/or for measuring the paint shade on structural surfaces, and/or for measuring the colour of surfaces coated with paints or enamels containing metal particles.

The invention will be described in detail with reference to the accompanying schematic drawings, in which:

FIG. 5 is a view of the portable testing head;

FIG. 6 is a view which illustrates colour measurements on a passenger car in a garage;

FIG. 7 is a modified embodiment of the testing head according to the invention;

Figure 1:
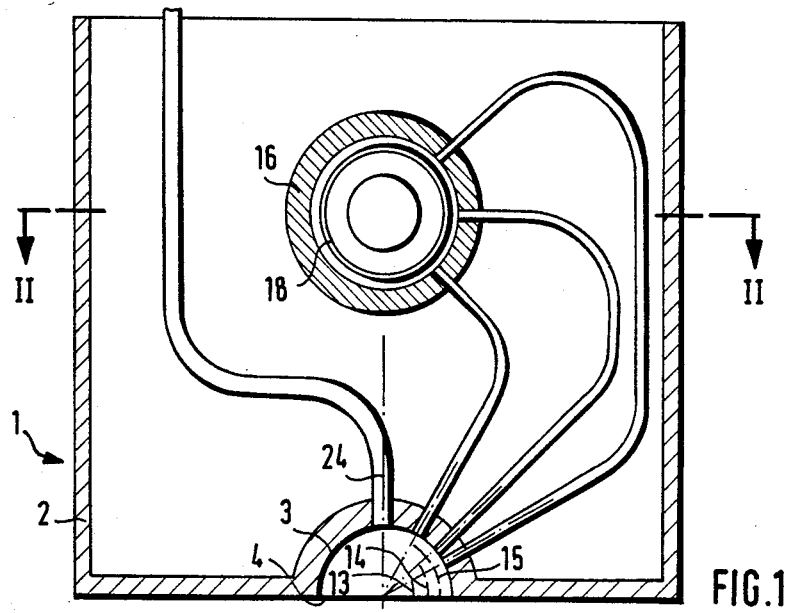
FIG. 1 is a cross-sectional view of the testing head according to the invention along the line I—I.
Figure 2:
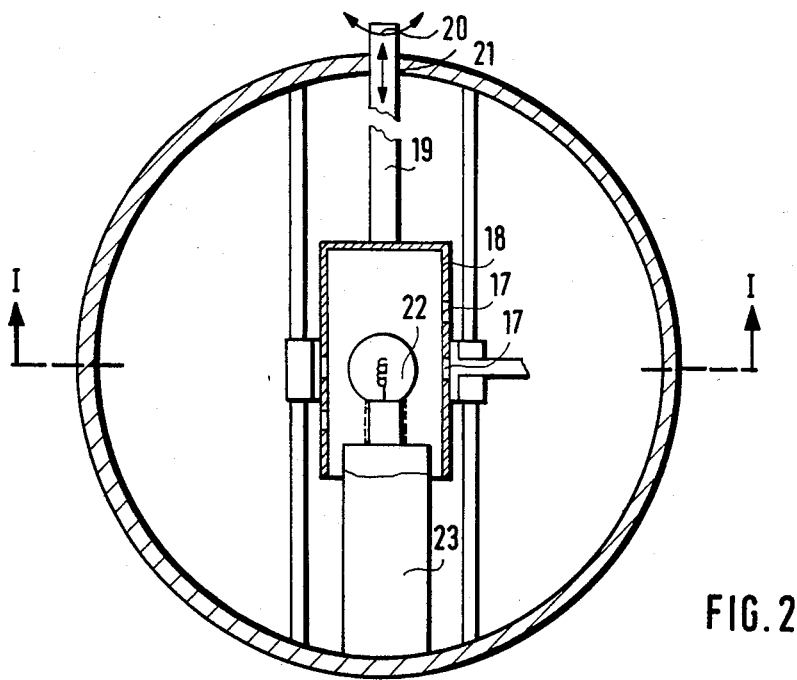
FIG. 2 is a sectional view of the testing head along the line II—II.
Figure 3:
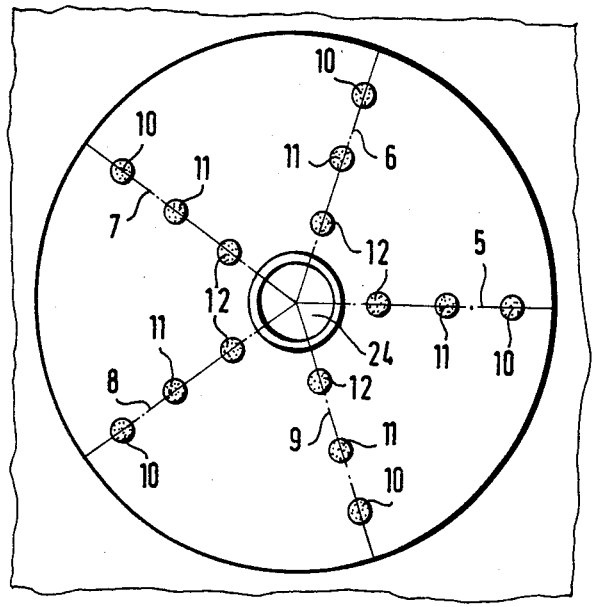
FIG. 3 is a view of the interior of the measuring cell on an enlarged scale.
Figure 4:
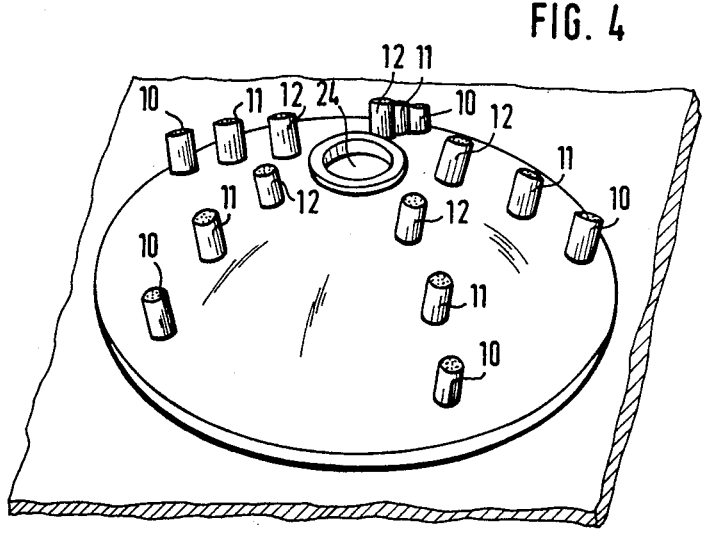
FIG. 4 is a partially perspective view of the outside of the measuring cell.

FIGS. 1 and 2 show partially and in section along the lines I and II, respectively, the essential parts of the testing head generally referred to by the numeral 1. The testing head 1 comprises a housing 2 formed at the underside thereof with a semispherical measuring cell 3 the open underside of which constitutes the measuring surface 4. In the embodiment shown in the FIGS. 3 and 4, the measuring cell 3 is provided in each of five different radial planes 5, 6, 7, 8, and 9 with three respective optical light guide members, which are optical fibre bundles 10, 11, and 12. In each of said five radial planes 5 to 9 the three optical fibre bundles 10, 11, and 12 are disposed at different angles 13, 14, and 15 of 15°, 30° and 70° relative to the measuring surface 4. Each of the optical fibre bundles known per se may comprise several hundreds of filaments. The ends of the optical fibre bundles 10, 11, and 12 which face away from the measuring cell terminate in a ring 16 fixedly mounted within the housing. Within the ring 16 there is provided a cylinder 18 provided with apertures 17, the cylinder 18 being rotatable about its axis 19 (see arrows 20) and axially movable (see arrows 21). The cylinder 18 constitutes an envelope for the single lamp 22 serving as light source, which is secured to the housing 2 by means of a support member 23. Depending on the position of the cylinder 18 the light emitted by the lamp 22 may be guide through predetermined optical fibre bundles 10, 11, and/or 12 to the measuring cell 3 to irradiate a sample disposed in the measuring surface 4. In the centre of the measuring cell 3 and perpendicular to the measuring surface 4 there is disposed an optical fibre bundle 24 for diverting the radiation reflected by the sample. The optical fibre bundle 24 shown in FIG. 4 is coupled to an electric analyzer 25, i.e., to a spectrophotometer, which has the following main functions:

Control function by means of a microprocessor for the testing head 1, detection and analysis of measurement data, transfer and printing of measurement data.

FIG. 5 shows the portable testing head 1, which is provided with a handle 26.

FIG. 6 shows that it is possible with the device according to the invention to measure in a simple manner and with great accuracy paint surfaces 27 on the spot, e.g. in a garage. The portable testing head 1 is placed on a cleaned, undamaged spot on the car to be painted. Then the measuring device is turned on after the measuring programme has been selected depending on the kind of sample and the type of paint. In accordance with the invention the preselected measuring programme may comprise, for instance, the following three measuring operations. In the first measuring operation the cylinder 18 and hence the apertures 17 are positioned such that the sample is irradiated only through the five optical fibre bundles 10 disposed at an angle of 15° to the measuring surface 4 and to the sample, and the radiation reflected from the sample is diverted via the optical fibre bundle 24 to the analyzer 25. In the second measuring operation the cylinder 18 and hence the apertures 17 are positioned such that the sample is irradiated only through the five optical fibre bundles 11 disposed at an angle of 30° relative to the measuring surface 4 and to the sample, and the radiation reflected from the sample is diverted via the optical fibre bundle 24 to the analyzer 25. In the third measuring operation the cylinder 18 and hence the apertures 17 are positioned such that the sample is irradiated only through the five optical fibre bundles 12 disposed at an angle of 70° relative to the measuring surface 4 and to the sample, and the radiation reflected from the sample is diverted via the optical fibre bundle 24 to the analyzer 25. Moreover, in accordance with the invention a measuring operation is possible in which irradiation occurs simultaneously at angles of $n \geqq 2$. Following the combination of the results of these measuring operations and a comparison with basic paint information stored in the system, the analyzer prints out a paint formulation which may be used for preparing the desired paint quantity and shade at the garage, for instance by means of a shade mixer, so that the desired paint may be applied.

Up to now paint formulations required for a given repair job have generally been prepared at garages by skilled persons to the best of their ability, mainly by a comparison of more or less similar paint cards. Such colour matching requires great skill and judgement. Experience has shown, however, that this procedure is not optimal and frequently leads to faulty results, i.e., unacceptable colour differences between the newly painted part of the vehicle body and the non-treated part.

The drawbacks of the method described above are eliminated with the use of the device according to the invention. Since it is possible when carrying out measurements with the device according to the invention to irradiate the sample successively at different angles and radial planes, measuring results will be obtained on the basis of which paint formulations may be prepared which lead to optimum results.

Instead of the aforementioned measuring programme various other measuring programmes may be used, in which three optical light guide means provided in the five radial planes in the present testing head may be turned on or off, respectively, either successively or partly simultaneously or all of them at once in any desired combination.

The measuring programme most suitable for each case should be chosen by the colour expert. As mentioned above, in the embodiment of the device according to the invention a desired measuring operation may be set by axial shifting and/or rotation of the cylinder 18. The surface of the cylinder 18 is provided with apertures 17 which correspond to the various optical light guide means and switching states. The cylinder 18 may simply be adjusted either manually or, if desired, by means of an electric motor which is controlled by the respective preselected measuring programme.

The embodiment described above employs in each radial plane three optical fibre bundles 10, 11 and 12 at angles of 15°, 30° and 70°. Within the scope of the invention it is also possible, however, to use different angles, e.g. angles of 20°, 45° and 75°. Furthermore, it is basically possible within the scope of the invention to provide in each radial plane optical fibre bundles which are not oriented at three but, for instance, at two, four, or five angles to the measuring surface.

FIG. 7 shows part of a variant embodiment of the measuring device according to the invention, in which like parts are referred to by like numerals. Here, the optical light guide means are formed in each radial plane by three lamps 28, 29, and 30, to which power is supplied via electric conductors 31, 32, and 33. This embodiment is provided with a total of 5×3=15 lamps 28, 29, and 30, which replace the optical fibre bundles. It should be added that the means referred to in the patent claims or anywhere else in this patent application as optical light guide means not merely comprise the use of optical fibre bundles but in particular also allow of the use of a plurality of lamps as shown in FIG. 7.

A further modification (see also FIG. 7) of the embodiments shown in FIGS. 1 to 4 consists in that the central means for diverting the radiation reflected from the sample is formed by an electrical conductor 34 which is mounted on the radiation receiving spot 36 of the measuring cell 3 by way of a converting element 35, which converts optical signals into electrical signals. This embodiment offers the advantage that a simple electrical conductor such as 34 is much better and less susceptible to interference than the described optical fibre bundle 24—especially in view of the fact that the measured values are to be transmitted over relatively long distances of, e.g., 5 to 25 meters.

In the embodiments of the invention as described, the irradiation of the sample is effected by means of optical fibre bundles 10, 11, and 12 and the viewing, i.e., diverting of the light rays reflected from the sample, is effected by means of optical fibre bundles 24. However, the device according to the invention is not limited to such an optical path. According to the invention, the optical path may basically be completely reversed. This means that an embodiment is conceivable in which the irradiation is effected successively by means of the optical fibre bundles 24 and 10, and the radiation reflected from the sample is diverted by means of the optical fibre bundles 11 and 12.

Furthermore, it should be noted that German Patent Specification No. 2,636,420 describes a chromatometer in which light diverting optical fibre bundles are provided in four different radial planes. Here, however, these optical fibre bundles are disposed at only a single angle of 45° to the measuring surface, so that this known device has only limited possibilities of use. Also, in this device the sample is irradiated and viewed through a glass plate, and the device is equipped with a sample elevating table, so that the device cannot readily be used for measurements on passenger cars.

Reference is also made to the paper "Die externe Integrationskugel—ein neuartiges Messgerät zur Oberflächen-Farbbestimmung" by Ernst Spreitzhofer, published in Chemie-Technik, reprint 9 (1980), 337–342 (Dr. Alfred Hüthig Verlag, Heidelberg). This paper describes a portable testing head, and section 3.4 of said paper describes and illustrates colour measurement on painted parts of a vehicle body by means of the portable testing head (FIG. 18). The testing head used in this instance comprises only a single diffuse and no direct illuminating means. Although it may be possible with this known device to obtain useful measuring results under relatively favourable conditions, this known testing head has the drawback that an optical fibre bundle is provided only in a single radial plane and at a single angle (of 45°) to the measuring surface, said optical fibre bundle being disposed adjacent the central optical fibre bundle which is oriented perpendicular to the measuring surface. Because of the limited measuring angle of the known testing head its practical use is not considered feasible for the measurement of paint shades, in particular when rather high demands are made as in the case of passenger cars.

Figure 8:
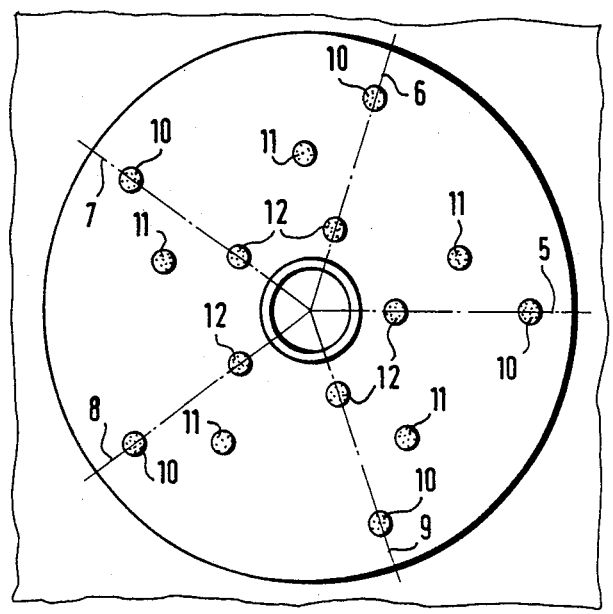
FIG. 8 is a view of the inside of the measuring cell of a modified embodiment.

In the modified embodiment of the measuring cell shown in FIG. 8 the three optical fibre bundles 10, 11 and 12 are disposed slightly off the radical planes.

Various modifications of the above-described and illustrated apparatus are possible within the scope of the present invention. For instance, the inside of the measuring cell need not be semispherical but may have some other shape.

What is claimed is:

1. A device for use in chromatometry of samples, such as colored surfaces, comprising: a testing head including a measuring cell having a measuring surface, the measuring cell comprising a plurality of optical light guide means disposed at different angles to the measuring surface and in different radial planes for supplying radiation irradiating said sample and at least one optical light guide means for diverting radiation reflected from said sample to an analyzing measuring means, wherein there is provided a switching system which enables fewer than all of the plurality of optical light guide means for supplying radiation to be selectively turned on and turned off.

2. The device of claim 1, wherein said switching system includes means for turning on and turning off a preselected number of said optical light guide means disposed at a preselected angle to said measuring surface.

3. The device of claim 1, comprising n (with n≧2) optical light guide means disposed at different angles to said measuring surface, wherein said switching system includes means for turning on and turning off all optical light guide means disposed at 1 to n−1 different angles to said measuring surface.

4. The device of claim 1, wherein the switching system includes means for turning on and turning off a preselected number of said optical light guide means disposed in at least one preselected radial plane.

5. The device of claim 1, wherein said optical light guide means are disposed in at least 3 different radial planes and at least 2 different angles to said measuring surface.

6. The device of claim 1, wherein an optical light guide means for diverting the radiation reflected from said sample is disposed in the centre of said measuring cell and vertical to said measuring surface, and wherein the remaining optical light guide means supply the radiation irradiating said sample.

7. The device of claim 1, wherein said optical light guide means are optical fibre bundles.

8. The device of claim 1, wherein said switching system comprises a switching means to which said optical light guide means are coupled and which includes means for turning on and turning off at least one of said optical light guide means.

9. The device of claim 1, wherein movable auxiliary means is provided for turning on and turning off at least one of said optical light guide means.

10. The device of claim 9, wherein said movable auxiliary means is formed by an axially movable envelope disposed between a light source and said optical light guide means and rotatable about its axis, the surface of said envelope being provided with at least one aperture for selectively exposing said optical light guide means to said light source.

11. The device of claim 1, wherein said measuring surface is directly irradiated.

12. The device of claim 1, wherein only a single light source is provided for irradiation, said light source being disposed within a portable testing head and being coupled thereto by means of optical fibre bundles.

13. The device of claim 1, wherein said measuring cell is provided for single-beam measurements of only single object, and wherein a reference object, such as a standard ceramic white plate, is disposed either externally or internally of said measuring cell.

14. The device of claim 1, wherein said means for diverting the radiation reflected from the sample is formed by an electrical conductor which is mounted on a particular radiation-receiving spot of said measuring cell by way of a converting element for converting optical signals into electric signals.

15. The device of claim 1, wherein said switching system permits turning on and turning off of at least a group of optical light guide means according to a preselected programme.

16. A device according to claim 5, wherein said optical light guide means are disposed in five different radial planes.

17. A method for measuring color of a colored surface comprising:
applying to said colored surface a measuring cell having a measuring surface, said measuring cell comprising a plurality of optical light guide means disposed at different angles to said measuring surface and in different radial planes for supplying radiation irradiating said colored surface and at least one optical light guide means for diverting radiation reflected from said surface to an analyzing measuring means, said measuring cell having associated therewith a switching system which enables fewer than all of the plurality of said optical light guide means for supplying radiation to be selectively turned on and turned off,
irradiating said surface by means of at least one of said plurality of optical guide means, and diverting radiation reflected from said surface to said analyzing measuring means by means of at least one of said plurality of optical light guide means.

18. A method according to claim 17, wherein one of said at least one optical light guide means for diverting said radiation reflected from said surface is disposed in the center of said measuring cell and vertical to said surface, and wherein remaining optical light guide means supply said radiation irradiating said surface.

19. A method according to claim 17, wherein movable auxiliary means are provided for turning on and turning off at least one of said optical light guide means.

20. A method according to claim 19, wherein said movable auxiliary means are formed by an axially movable envelope disposed between a light source and said optical light guide means and rotatable about its axis, said envelope being provided with at least one aperture which is selectively alignable with at least one of said optical light guide means.

21. A method according to claim 17, wherein only a single light source is provided for irradiation, said light source being disposed within a portable testing head and being coupled thereto by means of optical fiber bundles.

22. A method according to claim 17, wherein said colored surface is a body of a motor vehicle.

23. A method according to claim 17, wherein said colored surface is a structural surface.

24. A method according to claim 17, wherein said colored surface is coated with paint means.

25. A method according to claim 17, wherein said colored surface is coated with an enamel containing metal particles.

* * * * *